United States Patent [19]

Brace

[11] 3,989,725

[45] Nov. 2, 1976

[54] PERFLUOROALKYLTHIO NORBORNANE 2,3-DICARBOXYLIC ACID COMPOUNDS

[75] Inventor: Neal O. Brace, Wheaton, Ill.

[73] Assignee: Ciba-Geigy Corporation, Ardsley, N.Y.

[22] Filed: Aug. 29, 1975

[21] Appl. No.: 608,932

[52] U.S. Cl. .................... 260/346.3; 260/326 C; 260/455 R; 260/468 G; 260/502.6; 260/514 G; 260/544 L; 260/557 B
[51] Int. Cl.² ...................................... C07D 307/89
[58] Field of Search .......... 260/346.3, 468 G, 514 G

[56] References Cited
OTHER PUBLICATIONS

Claisse et al. J. Chem. Soc., 1965, p. 4894.
Claisse et al. J. Chem. Soc. (C), 1966, p. 1498.
Alden et al. J. Chem. Soc. (C), 1966, p. 1540.
Alden et al. J. Chem. Soc. (C), 1967, p. 1018.
Davies et al., J. Chem. Soc. (C), 1969, p. 1585.
Ludwick et al. J. Org. Chem., vol. 34, p. 4108, 1969.

*Primary Examiner*—Henry R. Jiles
*Assistant Examiner*—Bernard Dentz
*Attorney, Agent, or Firm*—Nestor W. Shust

[57] ABSTRACT

The compounds disclosed are of the formula

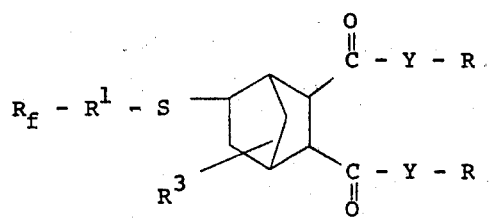

and the anhydrides thereof
wherein
  $R_f$ is a perfluoroalkyl group,
  $R'$ is a divalent group of alkylene, ether, thioether or a sec.amine,
  Y is oxygen, or an amine, and
  R is hydrogen or alkyl.
  $R^3$ is hydrogen or methyl These compounds can be prepared by a free radical catalyzed addition of a polyfluoroalkylthiol to a 5-norbornene diacid or its derivative. They are useful in preparing surfactants when reacted with an amine.

9 Claims, No Drawings

PERFLUOROALKYLTHIO NORBORNANE 2,3-DICARBOXYLIC ACID COMPOUNDS

DETAILED DISCLOSURE

The compounds of this invention are perfluoroalkylthio norbornane derivatives of the formulae

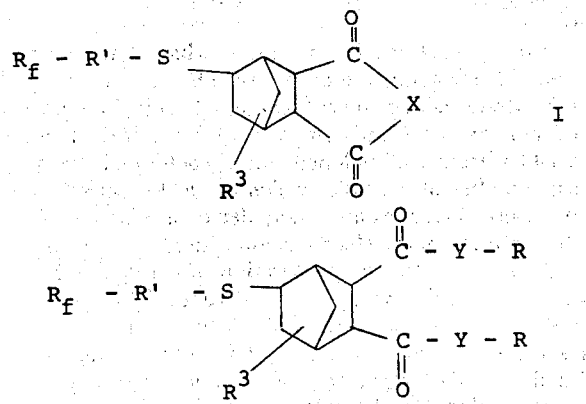

wherein
X is independently oxygen or the group >NR,
Y is independently oxygen, sulfur or the group >NR
R is independently hydrogen or alkyl of 1 to 24 carbons or each group - YR is independently a halogen
R' is a divalent radical of the formulae

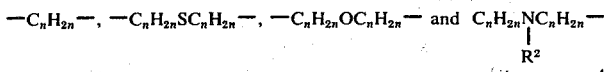

where $n$ is 1 to 12 and R' is hydrogen or alkyl of 1 to 6 carbons,
$R^3$ is hydrogen or methyl
$R_f$ is a straight or branched chain perfluoroalkyl of 1 to 18 carbon atoms or said perfluoroalkyl substituted by a perfluoroalkoxy group of 2 to 6 carbon atoms. $R_f$ can also be a mixture of perfluoroalkyl groups of 6–12 carbon atoms.

The anhydride or diacid compounds of this invention are useful in the preparation of perfluoroalkyl group containing polyesters or polyamides. In preparing these polymers the above compounds are employed as the known anhydrides and diacids. The anhydrides or diacid compounds, when converted to simple metal salts, show pronounced surface activity in aqueous media. Therefore they are useful as wetting or dispersion agents.

The exact nature of the group $R_f$ is not of critical importance as far as the compounds of this invention are concerned. For the sake of illustration, however, this group can be represented by such formulae as $—C_pF_{2p+1}$ and $C_8F_{28}OC_pF_{2p+1}$ where $p$ is 1 to 18 and preferably 6 to 12 and $q$ is 2 to 8.

The group R' is a divalent radical of the formulae

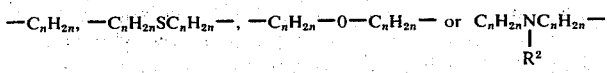

wherein
$n$ is 1 to 12 and preferably 1 to 4, $R^2$ is hydrogen or alkyl of 1 to 6 carbons. R' is preferably $—C_nH_{2n}—$ where $n$ is from 2 to 6.

The R groups are independently hydrogen or alkyl of 1 to 24 carbons and preferably of 1 to 6 carbons. Thus where Y is oxygen and both R groups are hydrogen the resulting compound is a dicarboxylic acid. If one R group is hydrogen and the other is alkyl, the resulting compound is a half ester, and when both R groups are alkyl, the compound is a diester. If Y is sulfur then the corresponding thioacids or thioesters results. When Y is an >NR group then an amido or an alkyl substituted amido compound results, depending on the definition of R.

Where X is oxygen the resulting compound is an anhydride and when it is >NR an imide is obtained. The compounds of formula II encompass acid halides when —YR is a halogen selected from chlorine, bromine or fluorine. Either both —YR groups can be acid halides or one —YR can be an ester, acid or amide while the other is an acid halide.

The above represented compounds can be obtained by a free radical catalyzed condition of a polyfluoroalkylthiol of the formula $R_f$-R'-SH to a 5-norbornene diacid, anhydride or a derivative thereof having a formula

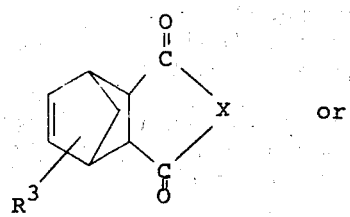 or 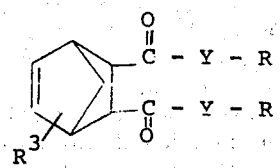

The norbornene reactant may have endo or exo cis configuration or it may have trans configuration when one —YR group is endo and the other exo. Therefore the compounds may exist in an isomeric mixture. The configuration of the norbornene reactant is normally retained in the addition product.

The various norbornene derivatives are available commercially. They can also be prepared by the methods described below.

The Diels-Alder addition of maleic anhydride to cyclopentadiene gives only the endo adduct, 5-norbornene-endo,endo-2,3-dicarboxylic anhydride. When dimethyl maleate is employed as the dienophile, the analogous reaction gives dimethyl 5-norbornene-endo,endo-2,3-dicarboxylate. Since the reaction is stereospecific, dimethyl fumarate or fumaric acid provides the corresponding trans-adducts. These unsaturated substances are the starting materials for the new products of this invention. Alternative routes to many of these starting materials are also known. For example, the esters may be made from the 5-norbornene-2,3-dicarboxylic anhydrides, or the trans-adducts may be obtained from the cis-adducts, by isomerization. There is only one known way to obtain the exo-anhydride, which is by isomerization of tne endo-anhydride, but from 5-norbornene-exo,exo-2,3-dicarboxylic acid anhydride the whole series of related derivatives may then be prepared.

The two alternative routes to exo-5-(1,1,2,2-tetrahydroperfluorodecylthio)-endo,endo-2,3-dicarboxylic acids are shown below:

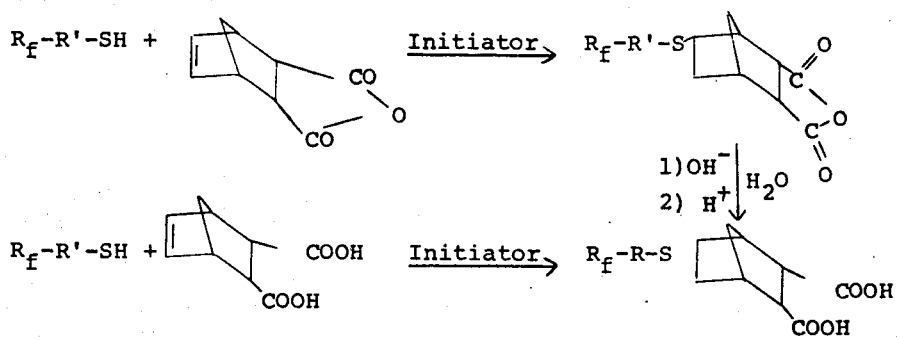

In a similar fashion the acids, esters, amides or alcohols of this invention can be prepared from the corresponding norbornene derivative in the manner most suitable to the purpose. The anhydride is particularly useful as it is readily converted to a large number of new compounds in high yield. There may be instances where the properties of the desired final product are such that it is more practical to follow one or the other procedure. Also, the precursor of the final product may be very difficult or impossible to prepare by a given route, but may be obtained by an alternate route. For example, the sodium salts of 5-norbornene-endo,endo-2,3-dicarboxylic acid are not readily obtained from the Diels-Alder reaction, but can be made from the adduct once the maleic anhydride-cyclopentadiene reaction has been done.

Other examples of the flexibility of approach which this invention affords, include the preparation of half esters either directly by radical addition of the perfluoroalkyl thiol to the norbornene dicarboxylic acid half ester, or by reaction of the exo-5-(1,1,2,2-tetrahydroperfluoroalkylthio)-norbornene-2,3-anhydride with an alcohol; or the preparation of exo-5-(1,1,2,2-tetrahydroperfluoroalkylthio)-norbornene-2,3-dicarboxylic acid imide either from the corresponding amic acid or directly by radical addition of the thiol to the imide, in analogy to the two paths shown above for the dicarboxylic acids.

Further variations in procedure which have been found advantageous are choice of solvent, reaction in bulk without added solvent, choice of radical initiator and reaction time and temperature. Of course, these variables are not all independent of each other. In the large number of examples which are in this specification, these variations are amply demonstrated.

Specific examples which describe alternate processes are Example 3, for the preparation of exo-5-(1,1,2,2-tetrahydroperfluorodecylthio)-endo,endo-2,3norbornane dicarboxylic acid, Examples 5 and 6 for the preparation of monomethyl ester of this acid and Examples 7 and 8 for the preparation of the imide of this acid.

The perfluoroalkyl thiols employed in the preparation of the compounds of this invention are well known in the prior art. For example, thiols of the formula $R_fR^1$—SH have been described in a number of U.S. patents including U.S. Pat. Nos. 2,894,991; 2,961,470; 2,965,677; 3,088,849; 3,192,190; 3,544,663 and 3,655,732.

Thus, U.S. Pat. No. 3,655,732 discloses mercaptans of formula

where $R^1$ is alkylene of 1 to 16 carbon atoms and $R_f$ is perfluoroalkyl and teaches that halides of formula $R_f$—$R^1$—hal are well known; reaction of $R_fI$ with ethylene under free-radical conditions gives $R_f(CH_2CH_2)_aI$ while reaction of $R_fCH_2I$ with ethylene gives $R_fCH_2(CH_2CH_2)_aI$ as is further taught in U.S. Pat. Nos. 3,088,849; 3,145,222; 2,965,659 and 2,972,638.

U.S. Pat. No. 3,655,732 further discloses compounds of formula

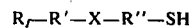

where

R' and R" are alkylene of 1 to 16 carbon atoms, with the sum of the carbon atoms of R' and R" being no greater than 25; $R_f$ is perfluoroalkyl of 4 through 14 carbon atoms and X is —S— or —NR'''— where R''' is hydrogen or alkyl of 1 through 4 carbon atoms.

U.S. Pat. No. 3,544,663 teaches that the mercaptan $R_fCH_2CH_2SH$ where $R_f$ is perfluoroalkyl of 5 to 13 carbon atoms, can be prepared by reacting the perfluoroalkyl alkylene iodide with thiourea or by adding $H_2S$ to a perfluoroalkyl substituted ethylene ($R_f$—CH=CH$_2$), which in turn can be prepared by dehydrohalogenation of the halide $R_f$—CH$_2$CH$_2$—hal.

The reaction of the iodide $R_f$—R$^1$—I with thiourea followed by hydrolysis to obtain the mercaptan $R_f$—R$^1$SH is the preferred synthetic route. The reaction is applicable to both linear and branched chain iodides. Many useful perfluoroalkoxyalkyl iodides are described in Australian Application No. 36963 filed Apr. 24, 1968, of general formula $(CF_3)_2CFO\ CF_2CF_2(CH_2CH_2)_mI$ where $m$ is 1—3.

Particularly preferred herein are the thiols of formula $R_fCH_2CH_2SH$ where $R_f$ is perfluoroalkyl of 6 to 12 carbon atoms. These $R_f$-thiols can be prepared from $R_fCH_2CH_2I$ and thiourea in very high yield.

Illustrative examples of preferred perfluoroalkylalkylenethiols are $C_4F_9CH_2SH$ $C_6F_{13}CH_2CH_2SH$ $C_8F_{17}CH_2CH_2SH$ $C_{10}F_{21}CH_2CH_2SH$ $C_{12}F_{25}CH_2CH_2SH$ $\begin{array}{c}CF_3\\ \phantom{CF}\searrow\\ \phantom{CF_3}CF_3\nearrow\end{array}CFO(CF_2CF_2)_{1\ to\ 3}\ CH_2CH_2SH$ Especially preferred perfluoroalkylalkylenethiols are $C_6F_{13}CH_2CH_2SH$ $C_8F_{17}CH_2CH_2SH$ $C_{10}F_{21}CH_2CH_2SH$ and mixtures thereof.

The free radical initiators that can be employed in the reaction are azo-nitriles and azo-derivatives which dissociate into alkyl- or aryl-radicals at reaction temperatures. The best known example of an azo-nitrile is 2,2'-azobisisobutyronitrile and the dissociation providing the required alkyl-radical is shown as follows:

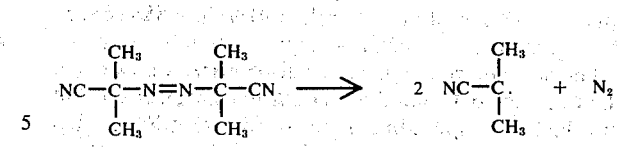

Other azo-nitriles are azo-derivatives which can be used are described in J. Brandrup and E. H. Immergut, Polymer Handbook (John Wiley & Sons) 1965 pages II-3 to II-14 and include, for example 2-cyano-2-propyl-aza-formamide
2,2'-azo-bis-isobytyronitrile
2,2'-azo-bis-2-methylpropionitrile
1,1'-azo-bis-1-cyclobutanenitrile
2,2'-azo-bis-2-methylbutyronitrile
4,4'-azo-bis-4-cyanopentanoic acid
1,1'-azo-bis-1-cyclopentanenitrile
2,2'-azo-bis-2-methylvaleronitrile
2,2'-azo-bis-2-cyclobutylpropionitrile
1,1'-azo-bis-1-cyclohexane nitrile
2,2'-azo-bis-2,4-dimethylvaleronitrile
2,2'-azo-bis-2,4,4-trimethylvaleronitrile
2,2'-azo-bis-2-benzylpropionitrile
1,1'-azo-bis-1-cyclodecane nitrile
azo-bis-(1-carbomethoxy-3-methylpropane)
phenyl-azo-diphenylmethane
phenyl-azo-triphenylmethane
azo-bis-diphenylmethane
3-tolyl-azo-triphenylmethane Certain peroxide-initiators can also be useful in preparing the compounds of the present invention. These peroxide-initiators als decompose instantly into alkyl- or aryl- radicals. The alkyl- or aryl- radical is obtained either by instantaneous decomposition or by a rearrangement reaction of the primary decomposition products of the peroxide compound. Of the peroxides, the aliphatic acyl peroxides are, for example, most useful and one preferred aliphatic peroxide is acetyl peroxide. The decomposition of this compound into alkyl-radicals can be set out as follows:

$CH_3COO\text{—}OCOCH_3 \xrightarrow{I} 2CH_3COO\cdot \xrightarrow{II} 2CH_3 + 2CO_2$ Reaction II follows Reaction I instantaneously. In the presence of iodine, only $CH_3I$ is isolated; proof of the instantaneous formation of the methyl radical. In addition to acetyl peroxide, lauroyl peroxide and decanoyl peroxides containing up to 18 carbon atoms are also useful as initiators. Such peroxide compounds include propionyl peroxide, butyryl peroxide, isobutryl peroxide, cyclobutaneacetyl peroxide, heptanoyl peroxide, caprylyl peroxide, cyclohexane acetyl peroxide, nonanoyl peroxide, myristoyl peroxide, stearyl peroxide and the like.

The free radical initiator is employed in the amounts of from 0.01 to 0.5 moles per mole of the norbornene starting compound and more preferably from 0.02 to 0.1 moles. The reaction is carried out at a temperature of from about 40° to about 150° C either in bulk or in an inert solvent which does not interfere with the reaction. Illustrative examples of appropriate solvents are hydrocarbon solvents such as benzene, toluene, cresol, xylene, cyclohexane, pentane, hexane. Other solvents that may be also employed are ethyl acetate, dioxane, acetone, dimethylformamide, dimethylsulfoxide, pyridine, dimethylsulfone, tetrahydrofuran, chloroform, nitrobenzene, cyclohexanone.

The addition reaction can be also carried out without the initiator, but then the reaction must be carried out at a higher temperature, such as 150° to 200° C. It is also possible to utilize ultraviolet radiation either alone or in combination with a free radical initiator. To accomplish the reaction under these conditions the reaction temperature may range from 10° to about 150° C.

Preferably the reaction is carried out in bulk, without a solvent medium, and in the presence of a free radical initiator, especially 2,2'-azo-bis-isobutyronitrile.

As noted above, 5-norbornene-2,3-endo, endo-dicarboxylic acid anhydride is available commercially. The corresponding esters can be prepared according to known methods, for example the dimethyl and the diethyl esters can be prepared by the method described by Morgan et al, *J. Am. Chem. Soc.* 66, 404 (1944) and Bauer et al., *J. Org. Chem.*, 26, 1106 (1961).

The half alkyl esters can be prepared by the method of L. M. Rice and E. E. Reid, *J. Am. Chem. Soc.*, 74, 3955 (1952), or H. M. Walton, *J. Org. Chem.*, 22, 308 (1957). 5-Norbornene-2,3-exo, endo-dicarboxylic acid can be prepared by the method of H. Koch, J. Kotlan and H. Markut, *Monatsh.*, 96, 1646 (1965) or of J. Sauer, H. Wiest and A. Mielert, *Chem. Ber.*, 97. 3183 (1964). N-phenyl, N-tolyl and N-benzylimides of 5-norbornene-2,3-endo, endo (or exo, exo)-dicarboxylic acids can be prepared by the method of M. S. Morgan, R. S. Tipson, A. Lowy and W. E. Baldwin, *J. Am. Chem. Soc.*, 66, 404 (1944). Many of these 5-norbornene-2,3-dicarboxylic acid derivatives can be prepared by the Diels-Alder reaction, as described by M. C. Kloetzel, *Org. Reactions*, Vol. IV, 1, (1948).

Presented below are examples to illustrate further the present invention without introducing any limitation.

EXAMPLE 1

Preparation of exo-5-(1,1,2,2-Tetrahydroperfluorooctylthio)-endo,endo-2,3-Norbornane Dicarboxylic Acid Anhydride In a 100 ml round bottom flask fitted with a nitrogen inlet tube, a reflux head connected to a cold trap, and stirred by magnet bar was placed 1,1,2,2-tetrahydroperfluorooctanethiol (20.0 g, 0.0526 mole), benzene (25 ml) and 5norbornene-2,3-endo, endo-dicarboxylic acid anhydride (8.20 g, 0.0500 mole). The solution was heated under a nitrogen atmosphere to 61° in an oil bath, as azobisisobutyronitrile (ABN, 0.284 g, 1.73 mmole) was added. The reaction temperature increased to about 70° C and was kept at 73°–76° C for 17 hours. The solid adduct was collected on a Buchner funnel, rinsed with ligroine and pressed dry. The filtrate was evaporated and the solid combined with the filtered solid. The yield of the product was quantitative. The product recrystallized from carbon tetrachloride had a m.p. of 103°–105° C and from ethyl acetate a m.p. of 107°–108° C. I.R. Spectrum and NMR were consistent with the structure of the above named compound.

Anal. Calcd for $C_{17}H_{13}F_{13}O_3S$: C, 37.51; H, 2.41; F, 45.38; S, 5.89. Found: C, 37.37; H, 2.27; F, 44.64; S, 5.75.

Table I below summarizes additional compounds prepared by the above described procedure, including the compound described above. Pure Adduct ($R_f = C_8F_{17}$, Example 4) was isolated directly from the reaction solvent, when a mixture of ethyl acetate and ligroine was used.

TABLE I

Preparation of exo-5-(1,1,2,2-Tetrahydroperfluoroalkylthio)-endo,endo-2,3-Norbornane Dicarboxylic Anhydrides.

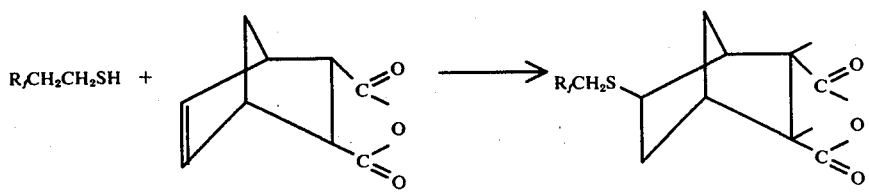

| | Reactants | | Conditions | | | | Product | | |
|---|---|---|---|---|---|---|---|---|---|
| | $R_fCH_2CH_2SH$ | Norbornene derivative | | ABN | | | | | |
| Example NO. | $R_f$ — wt mmol | wt mmol | Solvent ml | wt mmole | Time hr | Temp °C | Conv % | M.P. °C | Recrystallizing Solvent |
| 1 | $C_6F_{13}$ 20.0g (52.6) | 8.20g 50.0 | benzene 25 | 0.284g 1.73 | 17 | 73–76° | 100 | 107–108° | ethyl acetate |
| 2 | $C_6F_{13}$ 9.90g (26.04) | 4.10g 24.97 | benzene 20 | .0871g .531 | 5.2 | 74–80° | 100 | 107.5–108° | ligroine-ethyl acetate |
| 3 | $C_8F_{17}$ 9.60g (20.0) | 3.28g 20.0 | benzene 30 | .0821g .500 | 6 | 73–83° | 92 | 128–129° | benzene or ethyl acetate |
| 4 | $C_8F_{17}$ 96.04g (200.0) | 32.53 200.0 | EtAc(75 ml) ligroine (200ml) | 0.6568g 4.00 | 18 | 73–77° | 89 | 129–130° | (from reaction mixture) |
| 5 | $C_7F_{15}$ 6.25g (14.5) | 2.38g 14.5 | benzene 20 | .0821g .500 | 6 | 76–85° | 91 | 111–113.5° | benzene |
| 6 | $C_{10}F_{21}$ 29.07g (50.10) | 8.20°g 50.00 | benzene 50 | .164g 1.00 | 6 | 79–82° | 98 | 140–143° | ethyl acetate |
| 7 | $(CF_3)_2CFOCF_2CF_2$ 8.00g (23.1) | 3.79g 2.31 | benzene 25ml | .100g .609 | 6 | 69–74° | 100 | 85° | ligroine |
| 8 | $(CF_3)_2CFO(CF_2CF_2)_n$ n=6,8 (mixture) 12.0 g, (20.98mmole) | 3.44g 21.0 | benzene 20ml | 0.100g 0.609 | 6 | 70–82° | 93 | 91–94° | benzene |
| 9 | $CF_3(CF_2)n$ | 6.56g | benzene | .100g | 7 | 72–75° | 100 | 99–111° | |

TABLE I-continued

Preparation of exo-5-(1,1,2,2-Tetrahydroperfluoroalkylthio)-endo,endo-2,3-Norbornane Dicarboxylic Anhydrides.

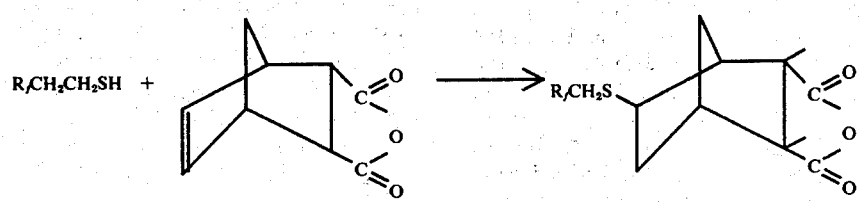

| Example NO. | Reactants | | | Conditions | | | | Product | | |
|---|---|---|---|---|---|---|---|---|---|---|
| | R$_f$CH$_2$CH$_2$SH | | Norbornene derivative | Solvent | ABN | Time | Temp | Conv | M.P. | Recrystallizing |
| | R$_f$ | wt mmol | wt mmol | ml | wt mmole | hr | °C | % | °C | Solvent |
| | | | 40.0 | | 45ml | .609 | | | (Unpurified) | | n=6,8,10
19.20g. (40.0 mmoles)
n=6, 3.80g (10.0 mmole)
n=8, 9.60g (20.0 mmole)
n=10, 5.80g (10.0 mmole)

EXAMPLES 10–12

Preparation of exo-5-(1,1,2,2-Tetrahydroperfluoroalkylthio)-exo,exo-2,3-Norbornane Dicarboxylic Acid Anhydrides Following the general procedure of Example 1 the adducts from the 1,1, 2,2-tetrahydroperfluoroalkanethiols and 5-norbornene-exo,exo-2,3-dicarboxylic acid anhydride were prepared, as listed in Table II. The exo anhydride was prepared from the endo anhydride as described below.

Part A (Preparation of the Anhydride)

solution was chilled to 5° C while stirring and the solid product (from 200 ml) collected and rinsed once with benzene at room temperature. The first crystal crop, wt. 25.65 g, mp. 125°–135°, was redissolved in 100 ml of benzene, and pure exo anhydride crystallized at room temperature as long shafts, wt. 16.64 g, mp. 139°–141.5°. Successive crystal fractions yielded 38.94 g. of additional exo anhydride. These fractions contained an increasing amount of endo anhydride and could be reheated to isomerize again to the exo isomer. The ratio of exo to endo was conveniently followed by integrated areas of proton resonances in the nmr spectra.

TABLE II

Preparation of exo-5-(1,1,2,2-Tetrahydroperfluoroalkylthio)-exo,exo-2,3-Norbornane Dicarboxylic Acid Anhydrides

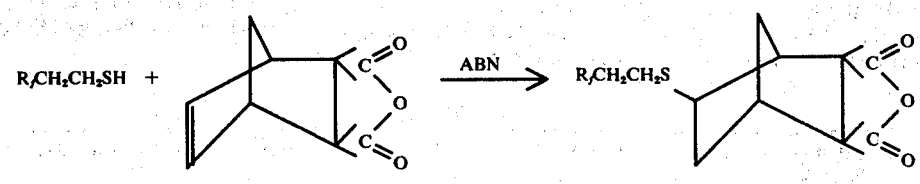

| Example No. | Reactants | | | Conditions | | | | | Product | |
|---|---|---|---|---|---|---|---|---|---|---|
| | R$_f$CH$_2$CH$_2$SH | | Norbornene derivative | Solvent | ABN | Time | Temp | Conv | | Recrystallizing |
| | R$_f$ | wt mmol | wt mmol | ml | wt mmol | hr | °C | % | M.P. | Solvent |
| 10 | CF$_3$(CF$_2$)$_n$ n=5,7,9 | 20.0g. (44.4) | 5.75g. 35.0 | benzene 25 ml | 0.100g. (.609) | 6 | 70–83° | 100 | 89–100° 79–91° | 11.13g 6.9g |
| 11 | CF$_3$(CF$_2$)$_7$ | 9.60g (20.0) | 2.96g | benzene 10 ml | 0.0821g. (0.500) | 5 | 67–73° | 95.8 | 104–106° | eth. acet./ ligroine |
| 12 | CF$_3$(CF$_2$)$_5$ | 7.60g (20.0) | 2.96g 18.0 | same | same | 5.5 | same | 93.7 | 72–73° | ligroine |

Isomerization of exo-5-Norbornene-endo,endo-2,3-Dicarboxylic Acid Anhydride to exo-5-Norbornene-exo,exo-2,3-Dicarboxylic Acid Anhydride —Following the procedure given by D. Craig, Journal of the American Chemical Society, Vol. 73, page 4889 (1951), the endo anhydride (76.5 g, 0.466 mol) was heated in a flask immersed in an oil bath at 180°–197° C, while stirring by a magnet bar under a slow purge of nitrogen, for 3 hours. Samples were removed after each hr. The hot, brown liquid was poured cautiously into 150 ml of benzene, a small amount of activated carbon added and after stirring for a few minutes, filtered while hot. The

EXAMPLE 13

Preparation of exo-5-(1,1,2,2-Tetrahydroperfluorodecylthio)-endo,endo-2,3-Norbornane Dicarboxylic Acid Following the procedure described in Example 1, 1,1,2,2-tetrahydroperfluorodecanethiol (9.60 g, 0.0200 mole), 5-norbornene-2,3-endo,endo-dicarboxylic acid (3.64 g, 0.0200 mole) and ABN (0.1200 g, 0.730 mole) were allowed to react in 50 ml of ethyl acetate. At 75° the solution became clear and it was kept at 73°–75° for 8 hours. The solvent was allowed to evaporate at room temperature and the solid (11.74 g, 89% of theory) melted over the range of 110°–130°. A portion of the solid product (1.2824 g, 1.936 mmol) was dissolved in 28.92 ml of 0.1000 N NaOH solution and 15 ml of ethanol at 40°. The foamy solution of the sodium salt was acidified with 5 ml of 6N HCl and the precipitated white solid acid was air dried (1.1545 g, 90% recovery, mp 133° C decomposition). Another portion of the product was recrystallized from ligroine containing sufficient ethyl acetate to clear the solution. Pure crystalline dicarboxylic acid was obtained melting at 137°–138° C (decomposition with gas evolution). IR and NMR spectra were consistent with the structure of the above-named compound.

The product was also prepared from the anhydride of Example 3 (Table I, Example 3, 1.2884 g, 2.000 mmol), sodium hydroxide (30.00 ml of 0.1000N solution, 3.000 mmol) and 5 ml of ethanol, heated at 40°–50° for 2 hr, acidified with 2.5 ml of 6N HCl; wt, 1.289 g, 100% yield, mp 117°–122°. An IR spectrum showed the COOH bands at 1710 and 1655 cm$^{-1}$.

Anal. Calcd for $C_{19}H_{15}F_{17}O_4S$: C, 34.45; H, 2.28; F, 48.77. Found: C, 34.36; H, 2.23; F, 48.29.

EXAMPLE 14

Preparation of exo-5-(1,1,2,2-Tetrahydroperfluorodecylthio)-exo,endo-2,3-Norbornane Dicarboxylic Acid Isomers, i.e., trans Diacid.

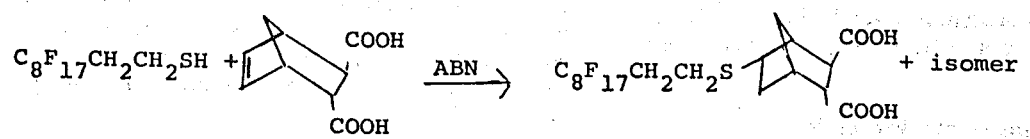

A mixture of 1,1,2,2-tetrahydroperfluorodecanethiol (12.00 g, 0.0250 mol), 5-norbornene-2-exo-3-endo-dicarboxylic acid (3.64 g, 0.0200 mol, mp 186°) and ABN (0.1200 g, 0.7000 mmol) were allowed to react in 25 ml of ethyl acetate. After 15 minutes at 72°–73° the slurry dissolved and an exotherm carried the temperature to 78°. After 2.5 hr at 75°–78° the clear solution was allowed to stand at 25°. Crystals of the product (4.806 g, mp 164°–166°) were collected. The hot filtrate was diluted with 15 ml of ligroine (bp 60°–70°) and when cool, deposited solid (8.274 g, mp 116°–128°, total yield, 100%).

Anal. Calcd for $C_{19}H_{15}F_{17}O_4S$: C, 34.45; H, 2.28; F, 48.77. Found: C, 34.28; H, 2.24; F, 48.83.

EXAMPLE 15

Preparation of Dimethyl 5-exo-(1,1,2,2-Tetrahydroperfluorooctylthio)-2,3-endo,endo-Norbornane Dicarboxylate A Fischer-Porter aerosol tube was charged with 1,1,2,2-tetrahydroperfluorooctanethiol (10.65 g, 0.02800 mole), dimethyl 5-norbornene-2,3-endo,endo-dicarboxylate (5.2 g, 0.0248 mole) and ABN (0.164 g, 1.00 mole), cooled to −78°, evacuated and filled with nitrogen three times and heated at 70.0° in an oil bath for 16 hr. From the reaction mixture 0.35 g of the thiol was recovered upon distillation at 125° C (0.10 mm). The remaining oil residue (14.8 g, 100% yield) was the desired product. IR and NMR spectra were consistent with the structure of the named compound.

Anal. Calc'd for $C_{19}H_{19}F_{13}O_4S$: C, 38.65; H, 3.24; F, 41.84; S, 5.48. Found: C, 38.32; H, 3.17; F, 41.46; S, 5.78.

In a similar fashion the following new acid esters of 5-exo-(1,1,2,2-tetrahydroperfluoroalkylthio)-x,x-2,3-norbornane dicarboxylic acid esters listed in Table III were prepared.

TABLE III

Preparation of exo-5-(1,1,2,2-Tetrahydroperfluoroalkylthio)-x-x-2,3-Norbornane Dicarboxylic Acid Esters

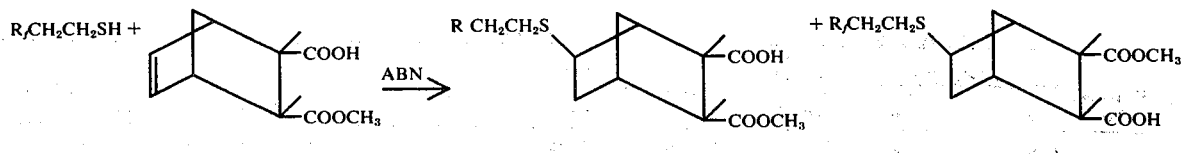

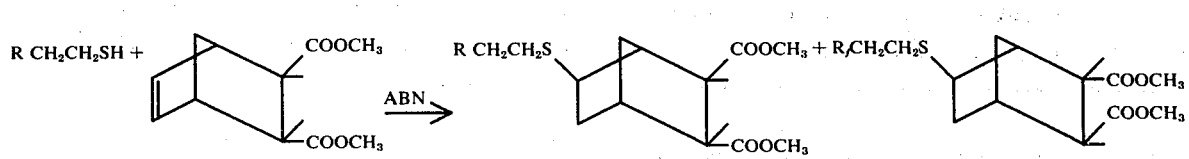

| Ex. No. | $R_fCH_2CH_2SH$ $R_F$ | wt mmol | Norbornene Derivative wt mmol | Solvent ml | ABN wt mmol | Time hr | Temp. °C | Conv. % | M.P. | Recrystallizing Solvent |
|---|---|---|---|---|---|---|---|---|---|---|
| 16 | $CF_3(CF_2)_n$ n=6,8,10 | 20.0 g (44.4) | 8.40 g (2b) (40.4) | neat | 0.100 g (0.609) | 6 | 70° | 97.5 | * | — |
| 17 | $CF_3(CF_2)_7$ | 10.0 g (20.8) | 4.20 g (2b) (20.0) | neat | 0.0500 g (0.345) | 13 | 69–74° | 94.5 | 65–69° | Ligroine |
| 18 | $CF_3(CF_2)_n$ n=6,8,10 | 20.0 g (44.4) | 7.85 g (2a) (40.0) | $CH_3OH$ 2.0 ml | 0.100 g (0.609) | 6 | 69–74° | 97 | 59–62° | — |

TABLE III-continued

Preparation of exo-5-(1,1,2,2-Tetrahydroperfluoroalkylthio)-x-x-2,3-Norbornane Dicarboxylic Acid Esters

| | Reactants | | | | Conditions | | | | Product | |
|---|---|---|---|---|---|---|---|---|---|---|
| Ex. No. | $R_fCH_2CH_2SH$ $R_F$ | wt mmol | Norbornene Derivative wt mmol | Solvent ml | ABN wt mmol | Time hr | Temp. °C | Conv. % | M.P. | Recrystallizing Solvent |
| 19 | $CF_3(CF_2)_7$ | 9.60 g (20.0) | 7.389 g (2a) (45.0) | $CH_3OH$ 10.0 ml | 0.125 g (0.761) | 6 | 75–78° | 100 | 74–85° | — |

EXAMPLE 20

Preparation of Methyl Hydrogen exo-5-(1,1,2,2-Tetrahydroperfluorodecylthio)-endo,endo-2,3-Norbornane Dicarboxylate Exo-5-(1,1,2,2-tetrahydroperfluorodecylthio)-endo,endo-2,3-norbornane dicarboxylic anhydride (Example 4, Table I, 12.88 g, 20.00 mmol) and methanol (32.0 g, 1.00 mol) were heated under reflux at 65° while stirring for one hour to give a clear solution of the half methyl ester. After standing several hours excess methanol was removed at the water pump, while heating to 72°. The white solid (13.21 g, 97.7% yield) melted over the range of 77°–85° and decomposed, gas evolving at 150°. Examination by IR and NMR spectra revealed that two isomers were present and that they were identical to the isomeric adduct mixture obtained by the alternate procedure given in Table III, Example 19.

Anal. Calc'd for $C_{20}H_{17}F_{17}O_4S$: C, 35.51; H, 2.53; F, 47.75. Found: C, 35.31; H, 2.49; F, 46.97.

EXAMPLE 21

Preparation of Methyl exo-5-(1,1,2,2-Tetrahydroperfluorodecylthio)-endo-Carboxylate-endo-N,N-Diethylamide The product of Example 20 (13.53 g, 20.0 mmol) and thionyl chloride (14.2 g, 120 mmol) was heated at 60° for 1 hour, and excess thionyl chloride removed at the water pump. The resulting intermediate acid chloride was divided in half. Benzene (30 ml) was added to half and at 5°, diethylamine (2.92 g, 40.0 mmol) was added slowly while stirring. After standing for 2 hours, the reaction mixture was worked up as in previous examples and the product isolated in 90.9% yield.

Analysis for $C_{24}H_{27}F_{17}NO_3S$: Calculated: C, 39.35; H, 3.72; F, 44.09; N, 1.91; S, 4.38. Found: C, 39.63; H, 3.46; F, 43.61; N, 1.92; S, 4.55.

EXAMPLE 22

Preparation of Methyl Hexylthio exo-5-(1,1,2,2-Tetrahydroperfluorodecylthio)-endo,endo-2,3-Dicarboxylate.

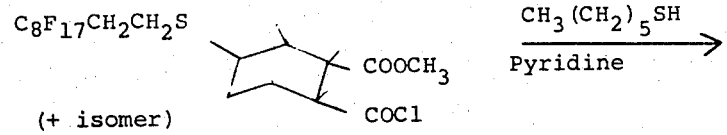

(+ isomer)

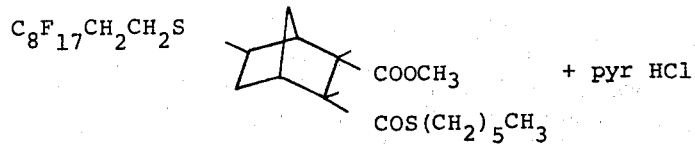

+ pyr HCl

15

To half of the acid chloride prepared above, benzene (30 ml) was added and at 10°, a solution of 1-hexanethiol (1.18 g, 1.40 ml, 10.0 mmol) and pyridine (0.791 g, 0.80 ml, 10.0 mmol) in benzene (10 ml) was slowly added while stirring. After heating at reflux temperature (78°) for 15 hrs. the solvent was removed by distillation and the product was recovered as a colorless liquid residue, 5.63 g (72.5% yield). The structure was confirmed by IR and NMR.

Analysis for: $C_{26}H_{29}F_{17}O_3S_2$: Calculated: C, 40.2; H, 3.76; F, 41.59; S, 8.26. Found: C, 41.4; H, 4.2; F, 40.0; S, 9.1.

EXAMPLE 23

Preparation of Hexylthio 5-exo-(1,1,2,2,-Tetrahydroperfluorodecylthio)-endo,exo-2,3-Dicarboxylate Exo-5-(1,1,2,2-tetrahydroperfluorodecylthio)-endo,exo-2,3-dicarboxylic acid (5.11g, 7.55 mmol) was converted to the endo, exo diacid chloride (5.10g). Benzene (30 ml) was added to the residual oil and a solution of 1-hexanethiol (1.80g, 15.1 mmol) and pyridine (1.20g, 1.20 ml, 15.1 mmol) in 10 ml of benzene was added slowly while stirring at 10°. After standing at room temperature for two hours the reaction mixture was filtered, rinsed with 10 ml of benzene and evaporated off to yield 3.6g of solid dihexylthio ester.

Analysis for: $C_{31}H_{39}F_{17}S_3O_2$: Calculated C, 43.15; H, 4.56; F, 37.4; S, 11.15. Found: C, 43.4; H, 4.8; S, 12.2.

EXAMPLE 24

Preparation of exo-5-(1,1,2,2-Tetrahydroperfluorodecylthio)endo,endo-2,3-Norbornane Dicarboxylic N,N-Diethylamide To the endo diacid chloride (5.10g, 7.55 mmol) prepared from the endo dicarboxylic acid of Example 13 is added benzene (30 ml), and while stirring at 5°, a solution of diethylamine (2.20 g, 0.0302 mol) in benzene (10 ml) is slowly added. After standing overnight at room temperature the mixture is filtered, washed with water, extracted with ether and the extract washed with 5% $Na_2CO_3$ solution and 2M HCl solution and dried over $MgSO_4$. The solvent is stripped off leaving a viscous oil.

EXAMPLE 25

Preparation of exo-5-(1,1,2,2-Tetrahydroperfluoroalkylthio)-endo,endo-2,3-Norbornane Dicarboxylic N,N-Diethylamides 5-Norbornene-endo,endo-2,3-dicarboxylic acid bis N,N-diethylamide, 2 is synthesized by the method of Koch, Kotlan and Markut, Monatshefte, 96, 1646 (1965). Following the general procedure of Example 15, free radical addition of a mixture of 1,1,2,2-tetrahydroperfluoroalkylthiols (19.20 g, 40.0 mmol) to the above prepared diethylamide (11.69 g, 40.0 mmol), initiated by ABN (0.100g, 0.609 mmol) in benzene (50 ml) at 70° for 8 hours gives solid product in good yield.

EXAMPLE 26

Preparation of exo-5-(1,1,2,2-Tetrahydroperfluoroalkylthio)exo,endo-2,3-Norbornane Dicarboxylic N,N-Diethylamides.

To the endo,exo-diacid chloride prepared in Example 23 (5.60g, 0.008 mol) in benzene (50 ml) was added diethylamine (2.91 g, 0.00400 mol) in benzene (10 ml) at 25°. After standing overnight at room temperature the mixture was filtered, washed with water, extracted with ether and the extract washed with 5% $Na_2CO_3$ solution and 2M HCl and dried over $MgSO_4$. The solvent was stripped off leaving a viscous oil (6.0 g, 97% yield) which solidified, m.p. 65°–68.5°.

Analysis for: $C_{27}H_{37}F_{17}N_2O_2S$: Calculated: C, 41.97; H, 4.30; F, 41.81; N, 3.63; S, 4.15. Found: C, 41.87; H, 4.25; F, 42.10.

What is claimed is:
1. A compound having the formula

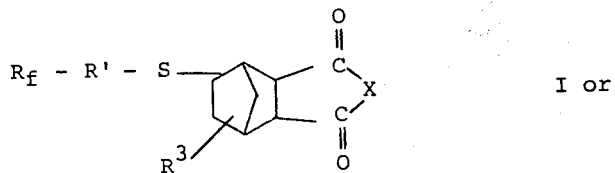

I or

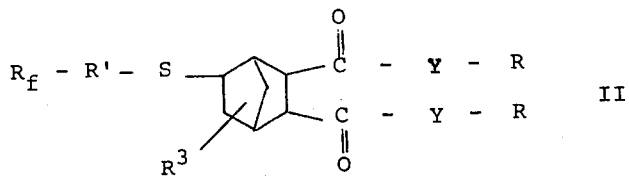

II and an isomeric mixture thereof, wherein
X is oxygen,
Y is oxygen,
R is independently hydrogen or alkyl of 1 to 24 carbons,
R' is a divalent radical of the formula

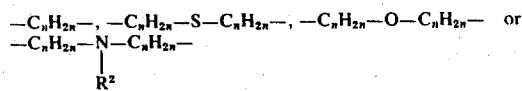

where *n* is 1 to 12 and $R^2$ is hydrogen or alkyl of 1 to 6 carbon atoms, $R_f$ is straight or branched chain perfluoroalkyl of 1 to 18 carbon atoms or said perfluoroalkyl substituted by perfluoroalkoxy of 2 to 6 carbon atoms, and $R^3$ is hydrogen or methyl.

2. A compound of claim 1 of formula I and an isomeric mixture thereof.

3. A compound of claim 1 of formula II wherein R is alkyl and an isomeric mixture thereof.

4. A compound of claim 2 wherein R' is $-C_nH_{2n}$.

5. A compound of claim 3 wherein R' is $-C_nH_{2n}$.

6. A compound of claim 4 wherein *n* is 2, $R_f$ is perfluoroalkyl group of 6 to 12 carbon atoms or a mixture of such groups and $R^3$ is hydrogen.

7. The compound of claim 6 which is exo-5-(1,1,2,2-tetrahydroperfluorooctylthio)-endo,endo-2,3-norbornane dicarboxylic acid anhydride.

8. The compound of claim 4 which is exo-5-(1,1,2,2-tetrahydroperfluorooctylthio)-endo,endo-2,3-norbornane dicarboxylic acid.

9. The compound of claim 1 which is dimethyl 5-exo-(1,1,2,2-tetrahydroperfluoroctylthio)-2,3-endo,endo-norbornane dicarboxylate.

* * * * *